(12) United States Patent
Shin et al.

(10) Patent No.: US 12,377,241 B2
(45) Date of Patent: Aug. 5, 2025

(54) SLEEP INDUCING DEVICE

(71) Applicant: LG ELECTRONICS INC., Seoul (KR)

(72) Inventors: Kangsoo Shin, Seoul (KR); Heenam Yoon, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 1065 days.

(21) Appl. No.: 17/420,829

(22) PCT Filed: Jan. 3, 2019

(86) PCT No.: PCT/KR2019/000116
§ 371 (c)(1),
(2) Date: Jul. 6, 2021

(87) PCT Pub. No.: WO2020/141641
PCT Pub. Date: Jul. 9, 2020

(65) Prior Publication Data
US 2022/0088346 A1 Mar. 24, 2022

(51) Int. Cl.
*A61M 21/02* (2006.01)
*A61M 21/00* (2006.01)

(52) U.S. Cl.
CPC ..... *A61M 21/02* (2013.01); *A61M 2021/0027* (2013.01); *A61M 2021/0088* (2013.01); *A61M 2205/50* (2013.01); *A61M 2230/42* (2013.01)

(58) Field of Classification Search
CPC .......... A61M 21/02; A61M 2021/0027; A61M 2021/0088; A61M 2205/50;
(Continued)

(56) References Cited

U.S. PATENT DOCUMENTS

2009/0062598 A1 3/2009 Haisma et al.
2011/0288431 A1 11/2011 Alshaer et al.
(Continued)

FOREIGN PATENT DOCUMENTS

| JP | 5437642 | 3/2014 |
|---|---|---|
| KR | 20130141289 | 12/2013 |
| KR | 101687321 | 12/2016 |

OTHER PUBLICATIONS

Ghanbari, A., Vaghei, Y., & Sayyed Noorani, S. M. R. (2014). Reinforcement Learning in Neural Networks: A Survey. International Journal of Advanced Biological and Biomedical Research, 2(5), 1398-1416 (Year: 2014).*

(Continued)

*Primary Examiner* — Sunita Reddy
(74) *Attorney, Agent, or Firm* — LEE, HONG, DEGERMAN, KANG & WAIMEY

(57) ABSTRACT

A sleep inducing device is disclosed. The sleep inducing device according to an embodiment of the present invention comprises: a sound output part for outputting a sound; a sensing part for acquiring a respiration signal of a user; and a processor which acquires a respiration frequency of the user on the basis of the respiration signal, determines a characteristic frequency of a respiration conforming sound on the basis of the respiration frequency, and outputs the respiration confirming sound according to the characteristic frequency.

14 Claims, 7 Drawing Sheets

(58) Field of Classification Search
CPC ...... A61M 2230/42; A61M 2205/0294; A61M 2205/42; A61M 2209/088; A61M 2230/40; A61B 5/08; A61B 5/0816; G10K 11/16
USPC .................................................. 600/26–28
See application file for complete search history.

(56) References Cited

U.S. PATENT DOCUMENTS

| | | |
|---|---|---|
| 2015/0367097 A1 | 12/2015 | Gavish |
| 2016/0151603 A1* | 6/2016 | Shouldice .............. A61B 5/486 600/26 |
| 2017/0312476 A1 | 11/2017 | Woo |
| 2019/0030278 A1* | 1/2019 | Kremer ................ A61B 5/4812 |
| 2019/0065970 A1* | 2/2019 | Bonutti .................. G16H 20/10 |
| 2020/0086076 A1* | 3/2020 | McElhone ......... G10K 11/1752 |

OTHER PUBLICATIONS

Machine Learning Algorithms: A Review; by Ayon Dey; Department of CSE, Gautam Buddha University, Greater Noida, Uttar Pradesh, India. Ayon Dey / (IJCSIT) International Journal of Computer Science and Information Technologies, vol. 7 (3) , 2016, 1174-1179 (Year: 2016).*

PCT International Application No. PCT/KR2019/000116, International Search Report dated Oct. 1, 2019, 6 pages.

* cited by examiner

SLEEP INDUCING DEVICE

CROSS-REFERENCE TO RELATED APPLICATIONS

This application is the National Stage filing under 35 U.S.C. 371 of International Application No. PCT/KR2019/000116, filed on Jan. 3, 2019, the contents of which are all hereby incorporated by reference herein in their entirety.

TECHNICAL FIELD

The present disclosure relates to a sleep induction device for determining a characteristic frequency based on the user's breathing frequency and outputting a breathing-tuned sound according to the characteristic frequency to induce a user's sleep.

BACKGROUND ART

Artificial intelligence is a field of computer engineering and information technology that research a method for allowing computers to do thinking, learning, self-development or the like that can be done by human intelligence, and means that computers is allowed to imitate human intelligent behavior.

In addition, the artificial intelligence does not exist by itself, but is directly or indirectly related to other fields of computer science. Especially, artificial intelligent factors have been introduced in the various field of information technology, and it has been actively attempted to utilize them to solve problems in the field.

Meanwhile, recently, a technique for inducing a user's comfortable sleep by reducing ambient noise using noise masking sound has emerged.

However, such a technology only removes factors that interfere with the user's sleep, and has a limitation because the technology cannot actively induce the user's sleep".

DETAILED DESCRIPTION OF THE INVENTION

Technical Problem

The present disclosure has been made to solve the above-mentioned problems occurring in the prior art, and an object of the present disclosure is to provide a sleep induction device for determining a characteristic frequency based on the user's breathing frequency and outputting a breathing-tuned sound according to the characteristic frequency to induce a user's sleep.

Technical Solution

According to an embodiment of the present disclosure, The sleep induction device according to an embodiment of the present disclosure may include a sound output unit for outputting a sound, a sensor for obtaining a user's breathing signal, and a processor for obtaining the user's breathing frequency based on the breathing signal, determining a characteristic frequency of breathing-tuned sound based on the breathing frequency, and outputting the breathing-tuned sound according to the characteristic frequency, wherein the characteristic frequency is a number of times a cycle of at least one of a magnitude and a frequency of the breathing-tuned sound is repeated for a unit time.

According to an embodiment of the present disclosure, a method for operating a sleep induction device includes obtaining a breathing signal of a user, obtaining a breathing frequency of the user based on the breathing signal, determining a characteristic frequency of a breathing-tuned sound based on the breathing frequency, and outputting the breathing-tuned sound according to the characteristic frequency, wherein the characteristic frequency is a number of times a cycle of at least one of a magnitude and a frequency of the breathing-tuned sound is repeated for a unit time.

Advantageous Effects of the Invention

The present disclosure can help the user to enter a sleep state quickly by inducing the user's breathing to gradually become slower using a sound having a characteristic frequency.

In addition, the present disclosure may reduce the characteristic frequency in a stepwise manner or reduce the characteristic frequency while maintaining a difference with the breathing frequency within a preset value to prevent a large difference from occurring between the user's actual breathing frequency and the frequency of the breathing-tuned sound and inducing a user to naturally breathe according to the breathing-tuned sound.

In addition, the present disclosure may achieve the effect of reducing ambient noise as well as inducing the user's breathing by combining a breathing inducing signal having a characteristic frequency with the noise masking sound, thereby further reducing the time for the user to enter the sleep state.

In addition, the present disclosure may have an advantage in that it is possible to find optimal values such as the timing of changing the characteristic frequency, the change amount of the characteristic frequency, the maximum magnitude of the breathing-tuned sound, and the type of the breathing-tuned sound by using reinforcement learning.

BEST MODE

Figure 1:
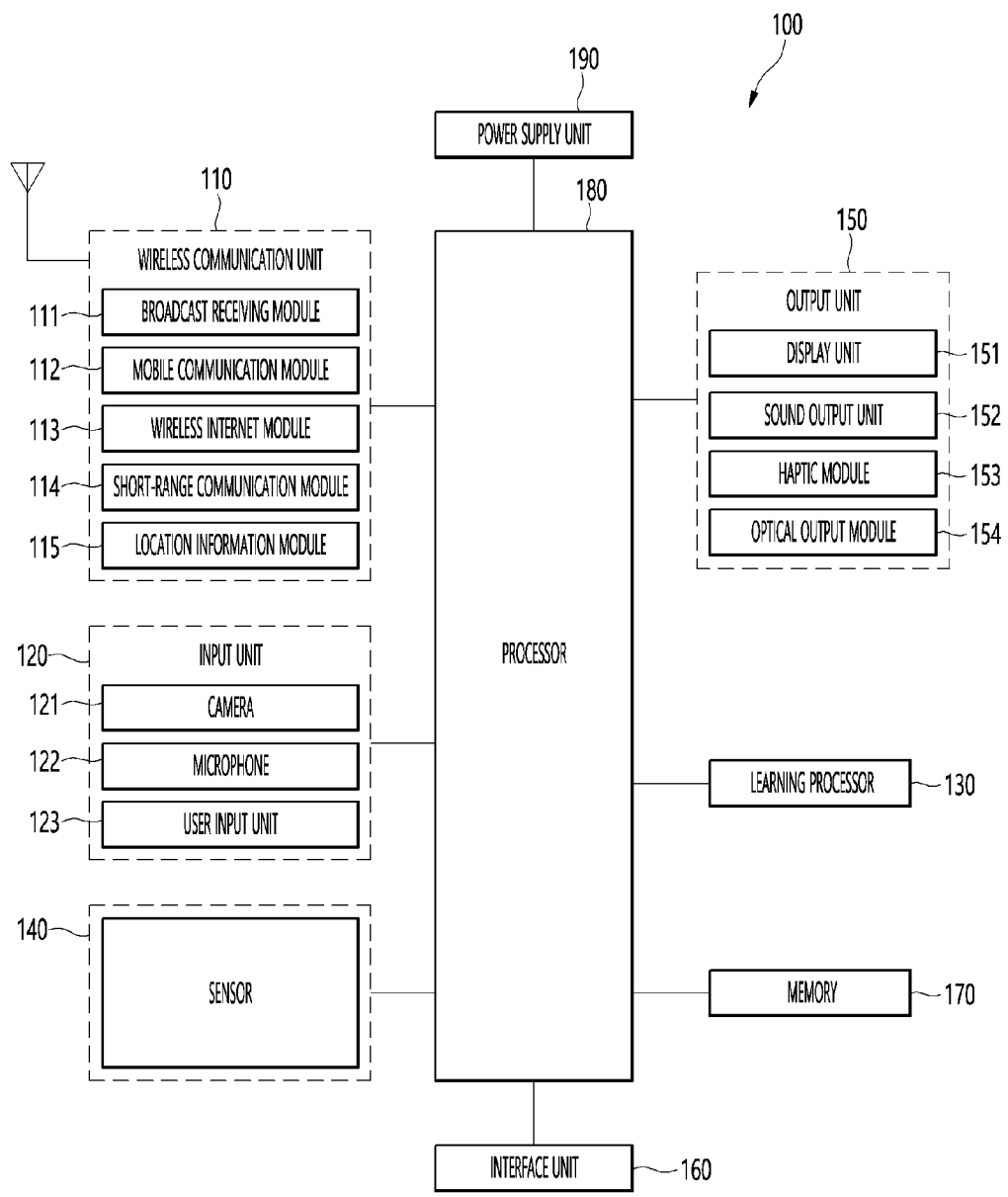
FIG. 1 is a block diagram for describing a sleep induction device related to the present disclosure.

Hereinafter, the embodiments disclosed herein will be described in detail with reference to the accompanying drawings, and the same or similar elements are designated with the same numeral references regardless of the numerals in the drawings and their redundant description will be omitted. The suffixes "module" and "unit or portion" for components used in the following description are merely provided only for facilitation of preparing this specification, and thus they are not granted a specific meaning or function. In addition, when it is determined that the detailed description of the related known technology may obscure the gist of embodiments disclosed herein in describing the embodiments, a detailed description thereof will be omitted. Further, the accompanying drawings are intended to facilitate understanding of the embodiments disclosed herein, and the technical spirit disclosed herein are not limited by the accompanying drawings. Therefore, the present invention should be construed as including all the changes, equivalents, and substitutions included in the spirit and scope of the present disclosure.

The terms coming with ordinal numbers such as 'first', 'second', or the like may be used to denote various components, but the components are not limited by the terms. The terms are used merely for the purpose to distinguish a component from the other component.

It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

A sleep induction device described herein may include mobile phones, smart phones, laptop computers, digital broadcasting terminals, personal digital assistants (PDAs), portable multimedia players (PMPs), navigation, slate PCs, Tablet PCs, ultra books, wearable devices, such as smartwatches, smart glass, or head mounted displays, and the like.

FIG. 1 is a block diagram for describing a sleep induction device related to the present disclosure.

A sleep induction device 100 according to embodiments described herein may be applied to a fixed terminal such as a smart TV, a desktop computer, a digital signage, or the like.

In addition, the sleep induction device 100 according to an embodiment of the present invention may be applied to a fixed or mobile robot.

Further, the sleep induction device 100 according to an embodiment of the present invention may perform a function of a speech agent. The speech agent may be a program that recognizes a user's speech and outputs a response suitable for the recognized user's speech with speech.

The sleep induction device 100 may include a wireless communication unit 110, an input unit 120, a learning processor 130, a sensor 140, an output unit 150, an interface unit 160, a memory 170, and a processor 180, and a power supply unit 190.

The wireless communication unit 110 may include at least one of a broadcast receiving module 111, a mobile communication module 112, a wireless Internet module 113, a short range communication module 114, and a location information module 115.

The broadcast receiving module 111 receives a broadcast signal and/or broadcast-related information from an external broadcast management server through a broadcast channel.

The mobile communication module 112 may transmit/receive a radio signal to/from at least one of a base station, an external terminal, and a server on a mobile communication network which is established according to a technical standard or a communication scheme for mobile communication (e.g., Global System for Mobile communication (GSM), Code Division Multi Access (CDMA), Code Division Multi Access 2000 (CDMA 2000), Enhanced Voice-Data Optimized or Enhanced Voice-Data Only (EV-DO), Wideband CDMA (WCDMA), High Speed Downlink Packet Access (HSDPA), High Speed Uplink Packet Access (HSUPA), Long Term Evolution (LTE), or LTE-A (Long Term Evolution-Advanced) and the like The wireless Internet module 113 refers to a module for wireless Internet access and may be provided inside or outside the sleep induction device 100. The wireless Internet module 113 is configured to transmit and receive wireless signals in communication networks according to wireless Internet technologies.

Examples of wireless Internet technologies include Wireless LAN (WLAN), Wireless-Fidelity (Wi-Fi), Wi-Fi Direct, Digital Living Network Alliance (DLNA), Wireless Broadband (WiBro), WiMAX (World Interoperability for Microwave Access (HSDPA), High Speed Downlink Packet Access (HSDPA), High Speed Uplink Packet Access (HSUPA), Long Term Evolution (LTE), and Long Term Evolution-Advanced (LTE-A).

The short range communication module 114 may support short-range communication using at least one of Bluetooth™, Radio Frequency Identification (RFID), Infrared Data Association (IrDA), Ultra Wideband (UWB), ZigBee, Near Field Communication (NFC), Wi-Fi (Wireless-Fidelity), Wi-Fi Direct, and Wireless USB (Wireless Universal Serial Bus) technologies.

The location information module 115 is a module for obtaining a location (or current location) of a mobile terminal, and a representative example thereof is a Global Positioning System (GPS) module or a Wireless Fidelity (WiFi) module. For example, when the terminal utilizes the GPS module, the terminal may acquire the location of the mobile terminal using a signal transmitted from a GPS satellite.

The input unit 120 may include a camera 121 for inputting an image signal, a microphone 122 for receiving an audio signal, and a user input unit 123 for receiving information from a user.

The speech data or image data collected by the input unit 120 may be analyzed and processed as a control command of the user.

The input unit 120 is for inputting image information (or signal), audio information (or signal), data, or information input from a user. In order to input image information, the sleep induction device 100 may include one or a plurality of cameras 121.

The camera 121 processes image frames such as still images or moving images obtained by an image sensor in a video call mode or a photographing mode. The processed image frames may be displayed on the display unit 151 or stored in the memory 170.

The microphone 122 processes external sound signals as electrical speech data. The processed speech data may be utilized in various ways according to a function (or running application program) being performed in the sleep induction device 100. Meanwhile, various noise reduction algorithms may be implemented in the microphone 122 to remove noise occurring in the process of receiving an external sound signal.

The user input unit 123 is for receiving information from the user, and when information is input through the user input unit 123, the processor 180 may control the operation of the sleep induction device 100 to correspond to the input information.

The user input unit 123 may include a mechanical input unit (or a mechanical key, for example, a button, a dome switch, a jog wheel, or a jog switch located at the front, rear, or side of the sleep induction device 100) and touch input means. As an example, the touch input means may include a virtual key, a soft key, or a visual key displayed on the touch screen through software processing, or a touch key disposed in the other portion than the touch screen.

The learning processor 130 may be configured to receive, classify, store, and output information to be used for data mining, data analysis, intelligent decision making, and machine learning algorithms and techniques.

The learning processor 130 may include one or more memory units configured to store data received, detected, sensed, generated, predefined, or outputted by the terminal, data received, detected, sensed, generated, predefined, or outputted in another method, or data outputted by another component, another device, another terminal or an apparatus communicating with the terminal.

The learning processor 130 may include a memory integrated or implemented in the terminal. In some embodiments, the learning processor 130 may be implemented using the memory 170.

Alternatively or additionally, the learning processor 130 may be implemented using a memory associated with the terminal, such as an external memory directly coupled to the terminal, or a memory maintained in a server communicating with the terminal.

In other embodiments, the learning processor 130 may be implemented using a memory maintained in a cloud computing environment or other remote memory locations accessible by the terminal via a communication scheme such as a network.

The learning processor 130 may be configured to store data in one or more databases to identify, index, categorize, manipulate, store, search, and output data for use in supervised or unsupervised learning, data mining, predictive analytics, or other machines.

The information stored in the learning processor 130 may be utilized by the processor 180 or one or more other controllers of the terminal using any of a variety of different types of data analysis algorithms and machine learning algorithms.

Examples of such algorithms may include k-nearest neighbors systems, fuzzy logic (e.g., probability theory), neural networks, Boltzmann machines, vector quantization, pulse neural networks, support vector machines, maximum margin classifiers, hill climbing, inductive logic systems Bayesian networks, Perritnets (e.g. finite state machines, Mealy machines, Moore finite state machines), classifier trees (e.g. perceptron trees, support vector trees, Markov trees, decision trees forests, arbitrary forests), stake models and systems, artificial fusion, sensor fusion, image fusion, reinforcement learning, augmented reality, pattern recognition, automated planning, and the like.

The processor 180 may determine or predict at least one executable operation of the terminal based on the determined or generated information using data analysis and machine learning algorithms. To this end, the processor 180 may request, search, receive, or utilize data of the learning processor 130. The processor 180 may control the terminal so as to execute a predicted operation or an operation determined to be desirable among the at least one executable operation.

The processor 180 may perform various functions for implementing intelligent emulation (that is, a knowledge based system, an inference system, and a knowledge acquisition system). This may be applied to various types of systems (e.g., fuzzy logic systems), including adaptive systems, machine learning systems, artificial neural networks, and the like.

The processor 180 may include sub-modules that enable computation involving speech and natural language speech processing, such as I/O processing module, environmental condition module, speech-to-text (STT) processing module, natural language processing module, workflow processing module and service processing module.

Each of these sub-modules may have access to one or more systems or data and models or a subset or superset thereof in the terminal. In addition, each of these sub-modules may provide a variety of functions, including lexical indexes, user data, workflow models, service models, and automatic speech recognition (ASR) systems.

In another embodiment, the processor 180 or other aspects of the terminal may be implemented with the sub-modules, systems, or data and models.

In some examples, based on data of the learning processor 130, the processor 180 may be configured to detect and sense requirements based on a user's intention or contextual conditions expressed by a user input or a natural language input.

The processor 180 may actively derive and obtain information necessary to fully determine a requirement based on a contextual condition or a user's intention. For example, the processor 180 may actively derive information necessary to determine requirements by analyzing historical data including historical inputs and outputs, pattern matching, unambiguous words, input intent, and the like.

The processor 180 may determine a task flow for executing a function in response to a requirement based on a context condition or a user's intention.

The processor 180 may collect, sense, extract, and detect and/or receive signals or data used for data analysis and machine learning operations through one or more sensing components in the terminal, in order to collect information for processing and storage in the learning processor 130.

Information collection may include sensing information through a sensor, extracting information stored in the memory 170, or receiving information from another terminal, an entity, or an external storage device through communication means.

The processor 180 may collect and store usage history information in a terminal.

The processor 180 may determine the optimal matching to perform a particular function using the stored usage history information and predictive modeling.

The processor 180 may receive or sense surrounding environment information or other information through the sensor 140.

The processor 180 may receive a broadcast signal and/or broadcast-related information, a wireless signal, and wireless data through the wireless communication unit 110.

The processor 180 may receive image information (or a corresponding signal), audio information (or a corresponding signal), data, or user input information from the input unit 120.

The processor 180 may collect information in real time, process or classify the information (e.g., knowledge graphs, command policies, personalization databases, dialog engines, etc.) and store the processed information in the memory 170 or the learning processor 130.

When an operation of the terminal is determined based on data analysis and machine learning algorithms and techniques, the processor 180 may control the components of the terminal to execute the determined operation. In addition, the processor 180 may execute the determined operation by controlling the terminal according to a control command.

The processor 180 may analyze historical information indicating the performance of a particular operation through data analysis and machine learning algorithms and techniques when the particular operation is performed, and perform update of previously learned information based on the analyzed information.

Accordingly, the processor 180 may improve data analysis and the accuracy of future performance of machine learning algorithms and techniques based on the updated information in cooperation with the learning processor 130.

The sensor 140 may include one or more sensors for sensing at least one of information in a mobile terminal, ambient environment information and user information of the mobile terminal.

For example, the sensor 140 may include at least one of a proximity sensor 141, an illumination sensor 142, a touch sensor, an acceleration sensor, a magnetic sensor, a G-sensor, a gyroscope sensor, a motion sensor, an RGB sensor, an infrared sensor (IR sensor), a finger scan sensor, an ultrasonic sensor, an optical sensors (e.g., cameras 121), a microphone 122, a battery gauge, environmental sensors (e.g., a barometer, a hygrometer, a thermometer, a radiation sensor, a thermal sensor, a gas sensor, etc.) and a chemical sensor (e.g., an electronic nose, a healthcare sensor, a biometric sensor, etc.) Meanwhile, the mobile terminal disclosed herein may utilize pieces of information sensed by at least two or more of these sensors by combining the pieces of information.

The output unit 150 is for generating an output related to sight, hearing, tactile, or the like, and may include at least one of a display unit 151, a sound output unit 152, a haptic module 153, and an optical output unit 154.

The display unit 151 displays (outputs) information processed by the sleep induction device 100. For example, the display unit 151 may display execution screen information of an application program running on the sleep induction device 100, or UI (User Interface) or Graphic User Interface (GUI) information according to the execution screen information.

The display unit 151 may implement a touch screen in such a manner that the display unit 151 forms a layer structure with or is integrally formed with a touch sensor. Such a touch screen may function as a user input unit 123 that provides an input interface between the sleep induction device 100 and the user and may provide an output interface between the sleep induction device 100 and the user at the same time.

The sound output unit 152 may output audio data received from the wireless communication unit 110 or stored in the memory 170 in call signal reception, a call mode or a recording mode, a speech recognition mode, a broadcast reception mode, or the like.

The sound output unit 152 may include at least one of a receiver, a speaker, and a buzzer.

The haptic module 153 generates various tactile effects that a user is able to feel. A representative example of the tactile effect generated by the haptic module 153 may be vibration.

The optical output unit 154 outputs a signal for notifying occurrence of an event by using light of a light source of the sleep induction device 100. Examples of events generated by the sleep induction device 100 may include message reception, call signal reception, a missed call, an alarm, schedule notification, email reception, and information reception through an application, and the like.

The interface unit 160 serves as a communicator with various types of external devices connected to the sleep inducing device 100. This interface unit 160 may include at least one of a wired/wireless headset port, an external charger port, a wired/wireless data port, a memory card port, a port for connecting a device equipped with an identification module, an audio I/O (Input/Output) port, a video I/O port, and an earphone port. The sleep induction device 100 may perform appropriate control related to a connected external device in response to the connection of the external device to the interface unit 160.

On the other hand, the identification module is a chip that stores a variety of information for authenticating the use authority of the sleep induction device 100, and may include a user identify module (UIM), a subscriber identity module (SIM), an universal subscriber identify module (USIM) and the like. A device equipped with an identification module (hereinafter referred to as an 'identification device') may be manufactured in a smart card form. Therefore, the identification device may be connected to the sleep induction device 100 through the interface unit 160.

The memory 170 may store data that supports various functions of the sleep induction device 100.

The memory 170 stores a plurality of application programs (or applications) running in the sleep induction device 100, data and instructions for operation of the sleep induction device 100, and data for the learning processor 130 (e.g., at least one piece of algorithm information for machine learning).

The processor 180 typically controls the overall operation of the sleep induction device 100 in addition to the operations associated with the application programs. The processor 180 may provide or process information or a function appropriate to a user by processing signals, data, information, and the like, which are input or output through the above-described components, or by executing an application program stored in the memory 170.

In addition, the processor 180 may control at least some of the components described with reference to FIG. 1 in order to execute an application program stored in the memory 170. In addition, the processor 180 may operate at least two or more of the components included in the sleep induction device 100 in a combination thereof to execute the application program.

The power supply unit 190 receives power from an external power source or an internal power source under the control of the processor 180 to supply power to each component included in the sleep induction device 100. The power supply unit 190 includes a battery, which may be a built-in battery or a replaceable battery.

As described above, the processor 180 controls the operations related to the application program, and the overall operation of the sleep induction device 100, generally. For example, when a state of the sleep induction device satisfies a set condition, the processor 180 may execute or release a lock state that restricts input of a user's control command to applications.

Meanwhile, the sensor 140 may include a wireless communication unit 110.

Figure 2:
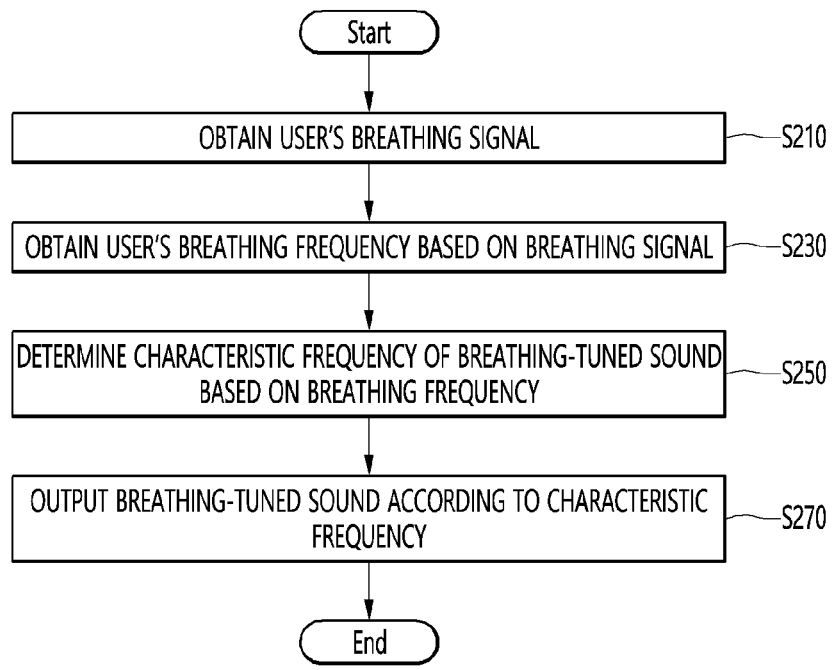
FIG. 2 is a diagram for describing a method of operating a sleep induction device, according to an embodiment of the present disclosure.

FIG. 2 is a diagram for describing a method of operating a sleep induction device, according to an embodiment of the present disclosure.

A method of operating the sleep induction device 100 according to an embodiment of the present disclosure may include obtaining a user's breathing signal (S210), obtaining a user's breathing frequency based on the user's breathing signal (S230), determining a characteristic frequency of a breathing-tuned sound based on the breathing frequency (S250) and outputting the breathing-tuned sound according to the characteristic frequency (S270).

Figure 3:
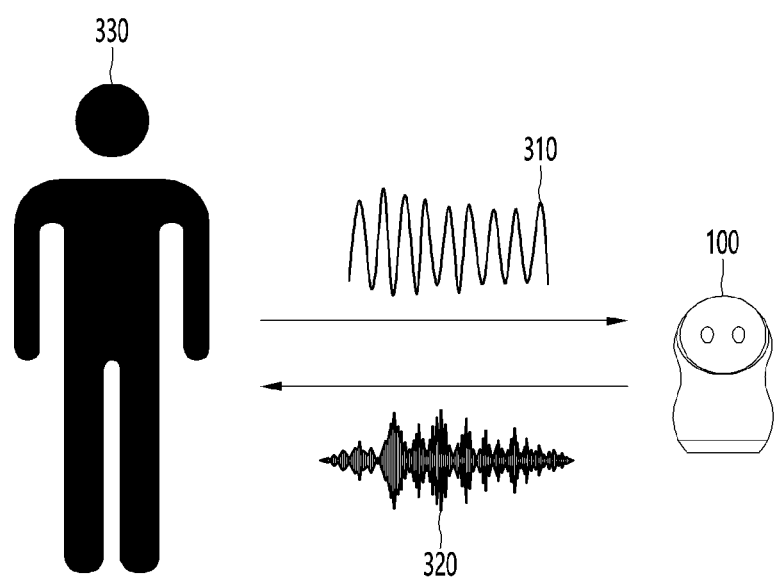
FIG. 3 is a diagram for describing breathing signal and a breathing-tuned sound according to an embodiment of the present disclosure.

FIG. 3 is a diagram for describing breathing signal and a breathing-tuned sound according to an embodiment of the present disclosure.

The processor 180 may obtain data related to the user's breathing through the sensor 140. Here, the data related to the user's breathing may be data used to measure the user's breathing signal.

For example, the data related to the user's breathing may be a detection value of a piezoelectric sensor. In this case, the piezoelectric sensor may be installed in a bed, and the processor 180 may communicate with the piezoelectric sensor to receive the detection value from the piezoelectric sensor. In this case, the detection value may vary according to the user's breathing signal.

As another example, the data related to the user's breathing may be a detection value of a belt. In this case, the belt may be worn on the user's body (chest), and the processor 180 may communicate with the belt to receive a detection value from the belt. In this case, the detection value may vary according to the user's breathing signal.

As another example, the data related to the user's breathing may be a measurement value of a radar sensor that detects the user's breathing. In this case, the processor 180 may communicate with the radar sensor to receive a measurement value from the radar sensor. In this case, the measurement value may vary according to the user's breathing signal.

In addition, any device capable of obtaining data related to the user's breathing may be used.

Meanwhile, although it has been described that data related to breathing is obtained from external devices such as a piezoelectric sensor, a belt, and a radar sensor, the present disclosure is not limited thereto. Specifically, an external device such as a piezoelectric sensor, a belt, or a radar sensor may obtain a breathing signal 310 using breathing-related data, and transmit the breathing signal 310 to the sleep induction device 100. In this case, the sensor 140 may receive the breathing signal 310 from an external device.

Meanwhile, a piezoelectric sensor, a belt, a radar sensor, and other devices capable of obtaining breathing-related data may be one component of the sensor 140 of the sleep induction device 100. In this case, the sensor 140 may directly obtain the user's breathing signal 310.

Meanwhile, the processor 180 may obtain a breathing frequency of the user based on the breathing signal 310 of the user. Here, the breathing frequency may mean the number of breathings per unit time.

Meanwhile, the breathing frequency of the user's breathing signal may be obtained based on the breathing signal during a preset time period. For example, the breathing frequency may be obtained based on the number of breathings from a time point 5 minutes before the current time point to the current time point.

In addition, the processor may determine the characteristic frequency of the breathing-tuned sound according to the breathing frequency of the user. The processor may output the breathing-tuned sound 320 according to the characteristic frequency.

Figure 4:
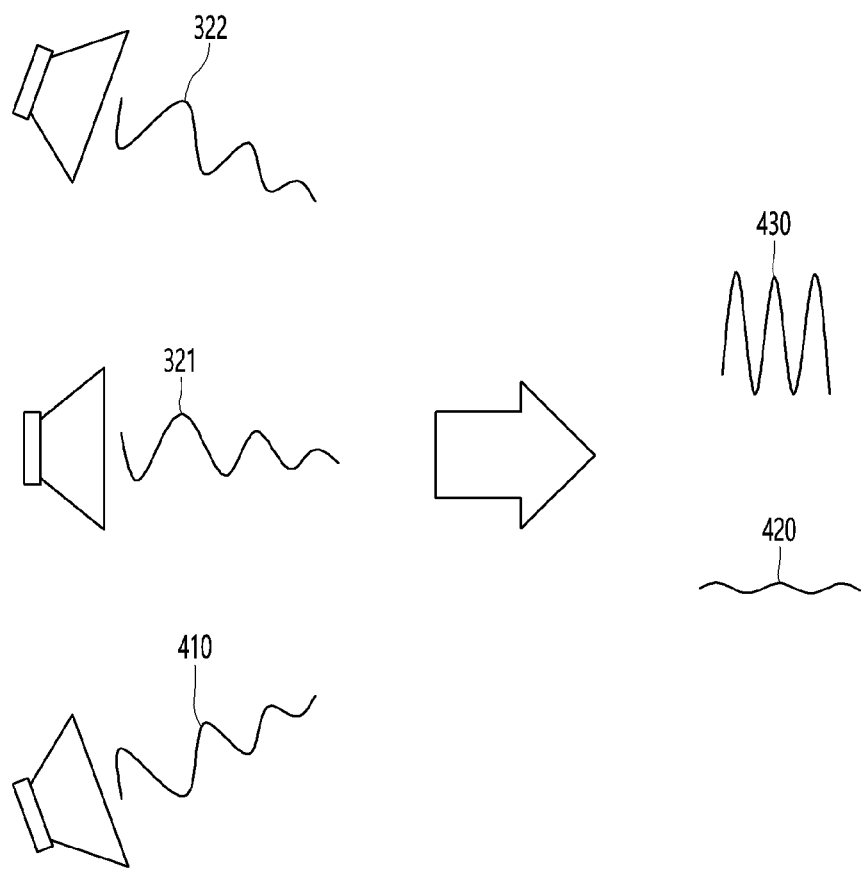
FIG. 4 is a view for describing in detail a breathing-tuned sound according to an embodiment of the present disclosure.

FIG. 4 is a view for describing in detail a breathing-tuned sound according to an embodiment of the present disclosure.

The breathing-tuned sound 320 may be a sound obtained by combining the breathing inducing sound 322 with noise masking sound 321.

Here, the noise masking sound 321 may be a sound for reducing an ambient noise 410. For example, the noise masking sound 321 may include white noise, pink noise, brown noise, and the like.

The breathing inducing sound 322 may be a signal inducing the user's breathing in order to induce the user's sleep.

Meanwhile, since the breathing-tuned sound 320 includes the noise masking sound 321, an ambient noise attenuation effect 420 may occur when the breathing-tuned sound 320 is combined with the ambient noise 410.

In addition, since the breathing-tuned sound 320 includes the breathing inducing signal 322, the breathing-tuned sound 320 may generate a breathing inducing effect 430 at the same time as generation of the ambient noise attenuation effect 420.

Figure 5A:
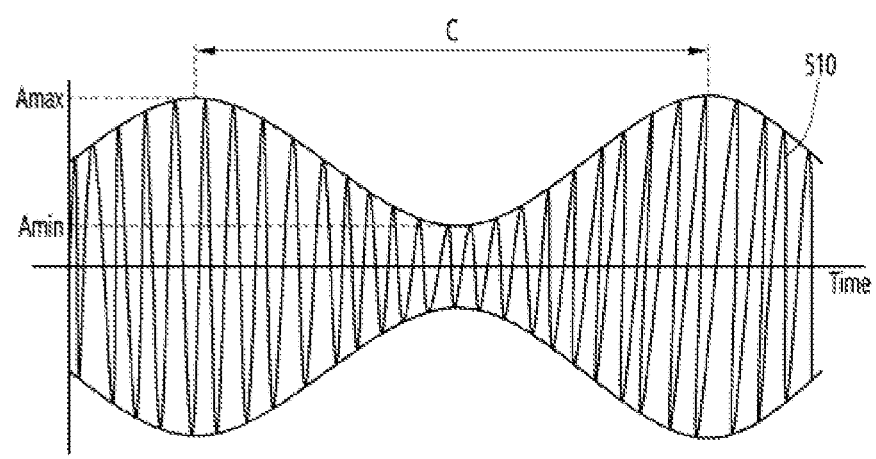
FIGS. 5A and 5B are diagrams for describing the magnitude, frequency, and characteristic frequency of a breathing-tuned sound, according to an embodiment of the present disclosure.
Figure 5B:
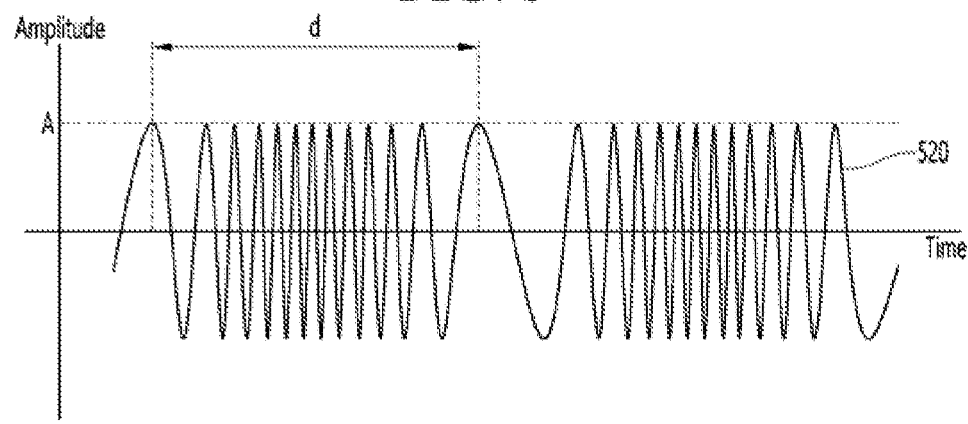

FIGS. 5A and 5B are diagrams for describing the magnitude, frequency, and characteristic frequency of a breathing-tuned sound, according to an embodiment of the present disclosure.

The characteristic frequency may be the number of times a cycle of at least one of a magnitude and a frequency of the breathing-tuned sound is repeated for a unit time.

In addition, the characteristic frequency may mean a frequency of a breathing inducing signal included in the breathing-tuned sound.

FIG. 5A is a diagram illustrating a cycle of the magnitude of a breathing-tuned sound.

The breathing-tuned sound 510 may be a sound obtained by changing the magnitude of a noise masking sound according to the breathing inducing signal. That is, the magnitude of the breathing-tuned sound 510 may be changed according to the breathing inducing signal.

Meanwhile, since the magnitude of the breathing inducing signal is changed in the form of a sine wave, the magnitude of the breathing-tuned sound 510 may be changed between the maximum value (Amax) and the minimum value (Amin).

On the other hand, a period (c) from the maximum value (Amax) to the next maximum value (Amax) of the magnitude of the breathing-tuned sound 510 may constitute one cycle.

As another example, a period from the minimum value (Amin) to the next minimum value (Amin) of the magnitude of the breathing-tuned sound 510 may constitute one cycle.

On the other hand, the characteristic frequency may be the number of times the cycle of the magnitude of the breathing-tuned sound 510 is repeated for a unit time.

For example, when the cycle of the magnitude of the breathing-tuned sound 510 is repeated 24 times for 1 minute, the characteristic frequency may be 24 breaths/min. In this case, the magnitude of the breathing-tuned sound 510 may reach the maximum value (Amax) or the minimum value (Amin) 24 times for one minute.

In addition, the cycle of the magnitude of the breathing-tuned sound 510 may be the same as the cycle of the breathing inducing signal. Therefore, a frequency of the breathing inducing signal may be the same as the characteristic frequency of the breathing-tuned sound 510.

On the other hand, in the embodiment of FIG. 5A, the frequency of the breathing-tuned sound 510 is the same, only the magnitude of the breathing-tuned sound 510 may be changed.

FIG. 5B is a diagram illustrating a cycle of the frequency of a breathing-tuned sound.

The breathing-tuned sound 520 may be a sound obtained by changing the frequency of a noise masking sound according to the breathing inducing signal. That is, the frequency of the breathing-tuned sound 520 may be changed according to the breathing inducting signal.

Meanwhile, according to the breathing inducing signal, the frequency of the breathing-tuned sound 520 may be changed between a maximum value and a minimum value.

On the other hand, a period (d) from the minimum value to the next minimum value of the frequency of the breathing-tuned sound 520 may constitute one cycle.

As another example, a period from the maximum value to the next maximum value of the frequency of the breathing-tuned sound 520 may constitute one cycle.

On the other hand, the characteristic frequency may be the number of times the cycle of the frequency of the breathing-tuned sound 520 is repeated for a unit time.

For example, when the cycle of the frequency of the breathing-tuned sound 520 is repeated 24 times for one minute, the characteristic frequency may be 24 breaths/min. In this case, the frequency of the breathing-tuned sound 520 510 may reach the maximum value or the minimum value 24 times for one minute.

In addition, the cycle of the frequency of the breathing-tuned sound 520 may be the same as the cycle of a breathing inducing signal. Therefore, the frequency of the respiratory inducing signal may be the same as the characteristic frequency.

Meanwhile, in the embodiment of FIG. 5B, the magnitude of the breathing-tuned sound 520 is constant and only the frequency of the breathing-tuned sound 520 may be changed. That is, since the magnitude of a noise masking sound is constant and only the frequency thereof is changed according to the breathing inducing signal, the magnitude of the breathing-tuned sound 520 may be constant.

On the other hand, although it has been described that the magnitude of the breathing-tuned sound is changed according to the breathing inducing signal in FIG. 5A and that the frequency of the breathing-tuned sound is changed according to the breathing inducing signal in FIG. 5B, the present disclosure is not limited thereto, and the magnitude and frequency of the breathing-tuned sound may be changed according to the breathing inducing signal.

In this case, the characteristic frequency may mean the number of times the cycle of the magnitude and frequency of the breathing-tuned sound is repeated for a unit time.

Meanwhile, the processor may change the characteristic frequency of the breathing-tuned sound.

Specifically, the period of one cycle may be changed according to the characteristic frequency of the breathing-tuned sound. That is, as the characteristic frequency increases, the time required to complete one cycle may be reduced (that is, the period may become shorter). Conversely, when the characteristic frequency decreases, the time required to complete one cycle may increase (that is the period may become longer).

Accordingly, as the processor changes the characteristic frequency of the breathing-tuned sound, the time (that is, period) required to complete at least one cycle of the magnitude or frequency of the breathing-tuned sound may be changed.

Meanwhile, the processor may determine the characteristic frequency of the breathing-tuned sound based on the breathing frequency.

In this case, the characteristic frequency of the breathing-tuned sound may be smaller than the breathing frequency.

Specifically, the breathing frequency during sleep of a person may be smaller than a normal breathing frequency (when the person is not drowsy).

Also, as the person enters sleep from normal (in a state where the person is not drowsy), the person's breathing frequency may gradually decrease.

In addition, a user who listens to the breathing-tuned sound may breathe naturally in synchronization with the characteristic frequency of the breathing-tuned sound. For example, in a case where the breathing frequency is 24 breaths/min because the user is not drowsy, when the breathing-tuned sound is output according to the characteristic frequency of 22 breaths/min, the user's breathing will be naturally induced at the frequency of 22 breaths/min.

Therefore, in the present disclosure, by decreasing the characteristic frequency to be smaller than the breathing frequency, it is possible to induce the user's breathing to be slow. As the user's breathing becomes slower, the time for the user to enter the sleep may be shortened.

On the other hand, although it has been described that the characteristic frequency is smaller than the breathing frequency, the characteristic frequency may be identical to the breathing frequency at some time points or in some periods in some cases.

Meanwhile, the maximum value of the characteristic frequency may be the user's normal breathing frequency. In addition, the minimum value of the characteristic frequency may be a breathing frequency during sleep of the user.

Here, the reason why the maximum value of the characteristic frequency is the user's normal breathing frequency is that the purpose of outputting the breathing-tuned sound is to induce the user's breathing slowly.

In addition, the reason why the minimum value of the characteristic frequency is the user's breathing frequency during sleeping is that the ultimate purpose of outputting a breathing-tuned sound is to induce the user's breathing to be the same as the user's breathing frequency during sleeping.

Meanwhile, the user's breathing information may be stored in the memory.

Specifically, the user's breathing information may be obtained based on the user's past breathing signals and stored in advance in the memory.

Here, the user's breathing information may include the user's normal breathing frequency (when the user is not drowsy) and the user's sleep breathing frequency.

Hereinafter, a process in which a user enters a sleep state after a sleep induction device starts to operate will be described in detail.

When a motion start input is received from a user or when it is detected that the user wants to go to bed by a sensor (when the user is lying in bed), the processor may start the operation of the sleep induction device.

In this case, the processor may output a breathing-tuned sound according to a first frequency.

Here, the first frequency may be identical to or smaller than the user's normal breathing frequency (when the user is not drowsy) pre-stored in the memory.

Meanwhile, the processor may reduce the characteristic frequency of the breathing-tuned sound.

Hereinafter, a first embodiment in which the characteristic frequency is changed in synchronization with the user's breathing frequency and a second embodiment in which the characteristic frequency is changed in a stepwise manner based on the user's breathing frequency will be described.

In the first embodiment, the processor may determine the characteristic frequency such that the difference between the characteristic frequency and the breathing frequency is maintained with in a preset value.

Specifically, the processor may decrease the characteristic frequency such that the difference between the characteristic frequency and the breathing frequency is maintained within the preset value.

For example, when the breathing frequency of the user's breathing signal is 24 breaths/min, the processor may output a breathing-tuned sound at a characteristic frequency of 22 breaths/min such that a difference between the breathing frequency and the characteristic frequency is maintained at 2 breaths/min. In addition, when the breathing frequency of the user's breathing signal is decreased to 22 breaths/min, the processor may output a breathing-tuned sound at a characteristic frequency of 20 breaths/min such that a difference between the breathing frequency and the characteristic frequency is maintained at 2 breaths/min.

In the second embodiment, the processor may decrease the characteristic frequency of the breathing-tuned sound in a stepwise manner based on the breathing frequency.

Specifically, the processor may change the characteristic frequency of the breathing-tuned sound from a first frequency to a second frequency smaller than the first frequency based on the breathing frequency, and output a breathing-tuned sound according to the second frequency.

In this case, the processor may determine the timing of changing the characteristic frequency from the first frequency to the second frequency based on the breathing frequency obtained while the breathing-tuned sound is being output according to the first frequency.

For example, it is assumed that the user is drowsy while the breathing-tuned sound is being output according to the first frequency, and the user's breathing frequency decreases. In this case, the processor may determine to change the characteristic frequency from the first frequency to the second frequency.

As another example, it is assumed that the breathing-tuned sound is output according to the first frequency, but the user is not drowsy, and the user's breathing frequency does not decrease. Even in this case, if the characteristic frequency is reduced, the difference between the user's current breathing frequency and the characteristic frequency becomes too large, making it difficult to induce the user's breathing.

Accordingly, in this case, the processor may continuously maintain the characteristic frequency as the first frequency. Then, when the user becomes drowsy and the breathing frequency of the user decreases, the processor may change the characteristic frequency from the first frequency to the second frequency.

On the other hand, the processor may output the breathing-tuned sound according to the first frequency, and when the difference between the user's breathing frequency and the first frequency becomes smaller within a predetermined magnitude, output the breathing-tuned sound according to the second frequency.

For example, it is assumed that the predetermined magnitude is 1 breath/min. In addition, it is assumed that the first frequency is 22 breaths/min, and the user's breathing frequency is 24 breaths/min when the sleep induction device is initially operated.

The processor may output a breathing-tuned sound according to a frequency of 22 breaths/min. When the user's breathing frequency decreases to 23 breaths/min, the processor may change the first frequency to the second frequency (e.g., 20 breaths/min).

Similarly, the processor may output the breathing-tuned sound according to the second frequency, and when the difference between the user's breathing frequency and the second frequency becomes smaller within a predetermined magnitude, output the breathing-tuned sound according to a third frequency smaller than the second frequency.

For example, the processor is outputting a breathing-tuned sound according to a frequency of 20 breaths/min. When the user's breathing frequency decreases to 21 breaths/min, the processor may change the second frequency to the third frequency (e.g., 18 breaths/min).

On the other hand, the processor may output the breathing-tuned sound according to the first frequency, and when the user's breathing frequency becomes the same as the first frequency, output the breathing-tuned sound according to the second frequency.

For example, it is assumed that the first frequency is 22 breaths/min, and the user's breathing frequency is 24 breaths/min when the sleep induction device is initially operated.

The processor may output a breathing-tuned sound according to a frequency of 22 breaths/min. When the user's breathing frequency decreases to 22 breaths/min, the processor may change the first frequency to the second frequency (e.g., 20 breaths/min).

Similarly, the processor may output the breathing-tuned sound according to the second frequency, and when the user's breathing frequency becomes the same as the second frequency, output the breathing-tuned sound according to a third frequency smaller than the second frequency.

For example, the processor is outputting a breathing-tuned sound according to a frequency of 20 breaths/min. When the user's breathing frequency decreases to 20 breaths/min, the processor may change the second frequency to the third frequency (e.g., 18 breaths/min).

Meanwhile, as a third embodiment, the processor may change the characteristic frequency of the breathing-tuned sound in a preset time unit, regardless of the breathing frequency while the breathing-tuned sound is being output.

Specifically, the processor may determine, as the characteristic frequency, the first frequency based on the user's breathing frequency stored in the memory, and output a breathing-tuned sound according to the first frequency.

When a preset time has elapsed since the breathing-tuned sound is output according to the first frequency, the processor may output the breathing-tuned sound according to a second frequency that is smaller than the first frequency.

When the preset time has elapsed since the breathing-tuned sound is output according to the second frequency, the processor may output the breathing-tuned sound according to a third frequency that is smaller than the second frequency.

Meanwhile, the change amount of the frequency may always be the same or may be different. For example, the first frequency may be 20 breaths/min, the second frequency may be 18 breaths/min, and the third frequency may be 16 breaths/min. As another example, the first frequency may be 20 breaths/min, the second frequency may be 18 breaths/min, and the third frequency may be 15 breaths/min.

Meanwhile, at least one of timing for changing a characteristic frequency and the change amount of the characteristic frequency may be determined by the reinforcement learning model.

Details will be described with reference to FIG. 7.

Before describing the change of the characteristic frequency using the reinforcement learning model, artificial intelligence (AI) will be briefly described.

Artificial intelligence is a field of computer engineering and information technology that research a method for allowing computers to do thinking, learning, self-development or the like that can be done by human intelligence, and means that computers is allowed to imitate human intelligent behavior.

In addition, artificial intelligence does not exist by itself, but is directly or indirectly related to other fields of computer science. Especially, artificial intelligent factors has been introduced in the various field of information technology, and it has been actively attempted to utilize them to solve problems in the field.

Machine learning is a field of research that gives computers ability to learn without explicit programming, as a branch of artificial intelligence.

Specifically, machine learning is a technique for researching and building a system that performs learning based on empirical data, performs predictions, and improves its own performance, and algorithms therefor. The algorithms in machine learning take a way of building specific models to derive predictions or decisions based on input data, rather than performing strictly defined static program instructions.

Many machine learning algorithms have been developed on how to classify data in machine learning. Decision trees, Bayesian networks, support vector machines (SVMs), and artificial neural networks are typical.

The decision trees are analytical methods that perform classification and prediction by charting decision rules in a tree structure.

The Bayesian network is a model that expresses the probabilistic relationship (conditional independence) between multiple variables in a graph structure. The Bayesian networks may be suited for data mining through unsupervised learning.

The support vector machine is a model of supervised learning for pattern recognition and material analysis, and is mainly used for classification and regression analysis.

The Artificial Neural Network (ANN) is a model of the connection between neurons and the principle of operation of biological neurons and is an information processing system in which a plurality of neurons called nodes or processing elements are connected in the form of a layer structure.

The Artificial Neural Network (ANN) is a model used in machine learning and an a statistical learning algorithm inspired by biological neural networks (especially the brain of the animal's central nervous system) in machine learning and cognitive science.

Specifically, the artificial neural network (ANN) may generally refer to a model having problem-solving ability in such a way that artificial neurons (nodes) constituting a network with synaptic bonding change the strength of synaptic bonding through learning.

The term "artificial neural network (ANN)" may be used interchangeably with the term "neural network".

The artificial neural network (ANN) may include a plurality of layers, and each of the layers may include a plurality of neurons. In addition, the artificial neural network (ANN) may include a synapse connecting neurons.

The artificial Neural Network (ANN) may be generally defined by the following factors: (1) patterns of connections between neurons of different layers, (2) a learning process of updating weights of connections, and (3) an activation function that takes a weighted sum of inputs received from previous layers to generate an output value.

The Artificial Neural Networks (ANNs) may include network models with the same schemes as Deep Neural Networks (DNNs), Recurrent Neural Networks (RNNs), Bidirectional Recurrent Deep Neural Networks (BRDNNs), Multilayer Perceptrons (MLPs), and Convolutional Neural Networks (CNNs), but are not limited thereto.

The Artificial Neural Networks (ANNs) are classified into Single Layer Neural Networks and Multi Layer Neural Networks according to the number of layers.

A typical single layer neural network consists of an input layer and an output layer.

Also, a typical multi layer neural network consists of an input layer, a hidden layer and an output layer.

The input layer is a layer that receives external materials. The number of neurons in the input layer is equal to the number of input variables. The hidden layer is located between the input layer and the output layer and receives signals from the input layer, extracts a feature, and transfers the same to the output layer. The output layer receives a signal from the hidden layer and outputs it to the outside. The input signals between neurons are respectively multiplied by connection strengths with a value between 0 and 1, and then summed. When the sum is greater than a threshold of the neuron, the neuron is activated and implemented as an output value through an activation function.

Meanwhile, a deep neural network (DNN), which includes a plurality of hidden layers between an input layer and an output layer, is a representative artificial neural network that implements deep learning that is a kind of the machine learning technology.

The Artificial Neural Networks (ANNs) may be trained using training data. Herein, training may refer to a process of determining a parameter of the artificial neural network (ANN) using training data in order to perform classification, regression, clustering, or the like on input data.

Representative examples of the parameter of the artificial neural network (ANN) may include weights assigned to synapses and biases applied to neurons. These parameters are internal parameters, and may be determined or updated through training of the artificial neural network (ANN).

Examples of parameters of the artificial Neural Network (ANN) may include the number of layers, the number of neurons, connectivity patterns between neurons in different layers, an activation function that takes a weighted sum of inputs received from previous layers to generate an output value. These parameters are external parameters and may be set by a user.

The artificial neural network trained by the training data may classify or cluster the input data according to a pattern of the input data.

Herein, the artificial neural network trained using the training data may be referred to as a trained model.

A learning method of the Artificial Neural Network (ANN) will be described below.

The learning method of the Artificial Neural Network (ANN) may be broadly classified into supervised learning, unsupervised learning, semi-supervised learning, and reinforcement learning.

The supervised learning is a kind of machine learning to infer a function from training data.

Among inferred functions as described above, to output a continuous value may refer to regression, and to predict and output a class of an input vector may refer to a classification.

In supervised learning, the artificial neural network (ANN) is trained in a state in which a label for training data is given.

Here, the label means a correct answer (or result value) that the artificial neural network (ANN) should infer when the training data is input to the artificial neural network (ANN).

In the present specification, when training data is input, the correct answer (or result value) that an artificial neural network (ANN) should infer is referred to as a label or labeling data.

In addition, in this specification, labeling the training data for the training of the artificial neural network (ANN) may be referred to as "labeling training data with labeling data".

In this case, the training data and a label corresponding to the training data constitute one training set, and may be input to the artificial neural network (ANN) in the form of the training set.

On the other hand, the training data represents a plurality of features, and the labeling of the training data with a label means may mean that the features represented by the training data are annotated with labels In this case, the training data may represent a feature of an input object in a vector form.

The artificial neural network (ANN) may infer a function of the correlation between the training data and the labeling data using the training data and the labeling data. In addition, the artificial neural network (ANN) may determine (optimize) the parameters of the artificial neural network (ANN) by evaluating the inferred function.

The unsupervised learning is a type of machine learning, and a label is not given to training data.

Specifically, the unsupervised learning may be a learning method for learning artificial neural networks to find out and classify patterns in the training data itself, rather than correlations between training data and labels corresponding to the training data.

Examples of the unsupervised learning may include clustering and independent component analysis.

Examples of artificial neural networks using the unsupervised learning may include a generative adversarial network (GAN) and an autoencoder (AE).

The Genetic Adversarial Network (GAN) is a machine learning method in which two different artificial intelligences, a generator, and a discriminator, compete with each other and improve performance.

In this case, the generator is a model for creating new data, and may generate new data based on original data.

In addition, the discriminator is a model for recognizing a pattern of data, and may discriminate the authenticity of the new data generated by the generator based on the original data.

In addition, the generator may receive and learn the data that did not deceive the discriminator, and the discriminator may receive and learn the deceived data from the generator. Accordingly, the generator may evolve to deceive the discriminator as best as possible, and may evolve to distinguish original data of the discriminator from the data generated by the generator.

The autoencoder (AE) is a neural network that aims to reproduce the input itself as an output.

The autoencoder (AE) includes an input layer, a hidden layer and an output layer, and the input data passes through the input layer and enters the hidden layer.

In this case, since the number of nodes in the hidden layer is less than the number of nodes in the input layer, the dimension of the data is reduced, and thus compression or encoding is performed.

Also, data output from the hidden layer enters the output layer. In this case, since the number of nodes in the output layer is greater than the number of nodes in the hidden layer, the dimension of the data is increased, and thus decompression or decoding is performed.

Meanwhile, an autoencoder (AE) may control the neuron's connection strength through learning, so that the input data is expressed as hidden layer data. In the hidden layer, information is represented by the smaller number of neurons than that in the input layer, and reproducing the input data as an output may mean that the hidden layer has found and expressed a hidden pattern from the input data.

The semi-supervised learning is a kind of machine learning, which may mean a learning method that uses both labeled training data and unlabeled training data.

One of schemes of the semi-supervised learning is to infer a label of unlabeled training data and then perform learning using the inferred label, which is useful when labeling cost is high.

Herein, an artificial neural network whose parameters are to be determined or to be continuously updated by performing learning through reinforcement learning may be referred to as a reinforcement learning model.

Meanwhile, the reinforcement learning model may be mounted on the sleep induction device 100.

On the other hand, the reinforcement learning model may be implemented in hardware, software, or a combination of hardware and software, and, when a part or whole of the reinforcement learning model is implemented in software, one or more instructions constituting the reinforcement learning model may be stored in memory.

The processor may provide the breathing frequency of the user as environment to the reinforcement learning model, output the breathing-tuned sound based on at least one of the timing at which the characteristic frequency is to be changed and the change amount of the characteristic frequency, which are recommended by the reinforcement learning model, and train the reinforcement learning model using a response of the user.

The reinforcement learning is a theory to find the best way through experience without data when given an environment in which an agent can decide what action to take at every moment.

Figure 6:
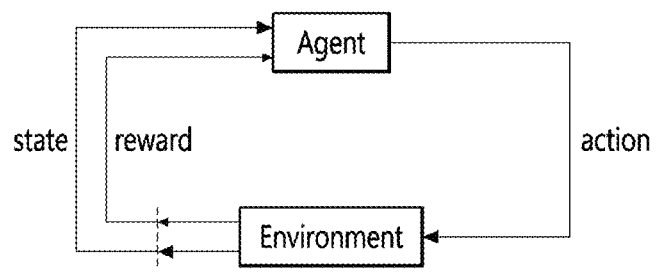
FIG. 6 is a diagram for describing the setting of a characteristic frequency using a reinforcement learning model according to an embodiment of the present disclosure.

The reinforcement learning may be performed primarily by the Markov Decision Process (MDP) as depicted in FIG. 6, for example.

To describe the Markov Decision Process (MDP), first, an environment is given in which the information necessary for the agent to take the next action is given, and secondly, how the agent will act in the environment is defined, third, what the agent will reward for doing well and penalty for not doing well are defined, and fourthly, the optimal policy is derived by iteratively undergoing experiences until the future reward reaches the highest point.

The Markov decision process is applied to the present disclosure, the agent may refer to a sleep induction device, more specifically, a reinforcement learning model.

First, in the present disclosure, an environment in which information necessary for the agent (reinforcement learning model) to take the next action are given, that is, the user's breathing frequency, may be given to the agent (reinforcement learning model).

Secondly, in the present disclosure, it is possible to determine how the agent (reinforcement learning model) will act using a given breathing frequency, that is, how to recommend at least one of timing for changing a characteristic frequency and the change amount of the characteristic frequency.

Thirdly, the processor may output a breathing-tuned sound according to at least one of timing at which the characteristic frequency recommended by the agent (reinforcement learning model) is changed and a change amount of the characteristic frequency. In addition, the processor may obtain the user's response corresponding to the outputted breathing-tuned sound. In addition, the processor may give a reward to the reinforcement learning model when the user's reaction is positive, and may give a penalty to the reinforcement learning model when the user's reaction is negative. In this case, the agent (reinforcement learning model) may update the parameters of the neural network based on the reward and the penalty.

Fourthly, the agent (reinforcement learning model) may repeat the experience until the future reward reaches the highest point to obtain the optimal policy, that is, 'at least one of the timing for changing the characteristic frequency and the change amount of the characteristic frequency' when the user's reaction becomes the most positive.

Here, the user's reaction may include at least one of a change in a user's breathing frequency, a user's movement, and a time required for the user to enter a sleep state.

The fact that the user's reaction becomes positive may mean that at least one of the change in the user's breathing frequency, the user's movement, and the time required for the user to enter the sleep state is changed to a state in which the user enters the sleep state quickly.

For example, a positive user reaction may include a decrease or a more rapid decrease in the user's breathing frequency, a decrease in the user's toss and downs, a decrease in the time required for the user to enter the sleep state, and the like.

In addition, the fact that the user's reaction becomes negative may mean that at least one of the change in the user's breathing frequency, the user's movement, and the time required for the user to enter the sleep state is changed to a state in which the user enters the sleep state slowly.

For example, a negative user reaction may include an increase in the user's breathing frequency, a decrease in the decrease width of the breathing frequency, an increase in the user's toss and downs, an increase in the time required for the user to enter the sleep state, and the like.

Meanwhile, in the previous embodiment, it has been described that the characteristic frequency is changed according to the breathing frequency. That is, the change of the breathing-tuned signal has been described on the assumption that the noise masking sound is always the same.

Hereinafter, the change of the noise masking sound together with the breathing-tuned signal will be described.

The processor may adjust the maximum magnitude of the breathing-tuned sound. Specifically, the processor may adjust the maximum magnitude of the breathing-tuned sound by changing the magnitude of the noise masking sound.

In this case, the processor may adjust the maximum magnitude of the breathing-tuned sound based on the environment information.

Here, the environmental information may include the magnitude of ambient noise. In this case, the processor may adjust the magnitude of the noise masking sound, that is, the maximum magnitude of the breathing-tuned sound based on the magnitude of ambient noise.

For example, the magnitude of ambient noise may be greater during the day than night. For another example, the magnitude of ambient noise may increase when music or television is being turned on. In this case, the processor may maximize the noise masking effect by adjusting the magnitude of the noise masking sound, even when the magnitude of the ambient noise changes.

Meanwhile, it has been previously described that the breathing frequency is provided to the reinforcement learning model as an environment, and the reinforcement learning model recommends at least one of timing for changing a characteristic frequency and a change amount of the characteristic frequency.

As another embodiment, the reinforcement learning model may determine at least one of the timing for changing the characteristic frequency, the change amount of the characteristic frequency, the maximum magnitude of the breathing-tuned sound, and the type of the breathing-tuned sound (e.g., white noise, pink noise, brown noise, etc.) by additionally considering environmental information.

Specifically, the processor may provide the user's breathing frequency and environmental information as an environment to the reinforcement learning model, output breathing-tuned sound based on 'at least one of the timing for changing the characteristic frequency, the change amount of the characteristic frequency, the maximum magnitude of the breathing-tuned sound, and the type of the breathing-tuned sound' and train the reinforcement learning model using the user's reaction.

When the Markov Decision Process is applied to this embodiment, first, an environment in which information necessary for the agent (reinforcement learning model) to take the next action are given, that is, the user's breathing frequency and environmental information (the magnitude of ambient noise, the type of ambient noise, or the like) may be given to the agent (reinforcement learning model).

Secondly, in the present disclosure, it is possible to determine how the agent (reinforcement learning model) will act using a given breathing frequency and environmental information, that is, how to recommend at least one of timing for changing a characteristic frequency, the maximum magnitude of the breathing-tuned sound, and the type of the breathing-tuned sound.

Thirdly, the processor may output a breathing-tuned sound according to 'at least one of timing for changing a characteristic frequency, the maximum magnitude of the breathing-tuned sound, and the type of the breathing-tuned sound' recommended by the agent (reinforcement learning model) is changed and a change amount of the characteristic frequency. In addition, the processor may obtain the user's response corresponding to the outputted breathing-tuned sound. In addition, the processor may give a reward to the reinforcement learning model when the user's response is positive, and may give a penalty to the reinforcement learning model when the user's response is negative. In this case, the agent (reinforcement learning model) may update the parameters of the neural network based on the reward and the penalty.

Fourthly, the agent (reinforcement learning model) may repeat the experience until the future reward reaches the highest point to determine the optimal policy, that is, 'at least one of timing for changing a characteristic frequency, the maximum magnitude of the breathing-tuned sound, and the type of the breathing-tuned sound' when the user's response becomes the most positive.

As described above, the present disclosure can help the user to enter a sleep state quickly by inducing the user's breathing to gradually become slower using a sound having a characteristic frequency.

In addition, the present disclosure may reduce the characteristic frequency in a stepwise manner or reduce the characteristic frequency while maintaining a difference with the breathing frequency within a preset value to prevent a large difference from occurring between the user's actual breathing frequency and the frequency of the breathing-tuned sound and inducing a user to naturally breathe according to the breathing-tuned sound.

In addition, the present disclosure may achieve the effect of reducing ambient noise as well as inducing the user's breathing by combining a breathing inducing signal having a characteristic frequency with the noise masking sound, thereby further reducing the time for the user to enter the sleep state.

In addition, the present disclosure may have an advantage in that it is possible to find optimal values such as the timing of changing the characteristic frequency, the change amount of the characteristic frequency, the maximum magnitude of the breathing-tuned sound, and the type of the breathing-tuned sound by using reinforcement learning.

Figure 7:
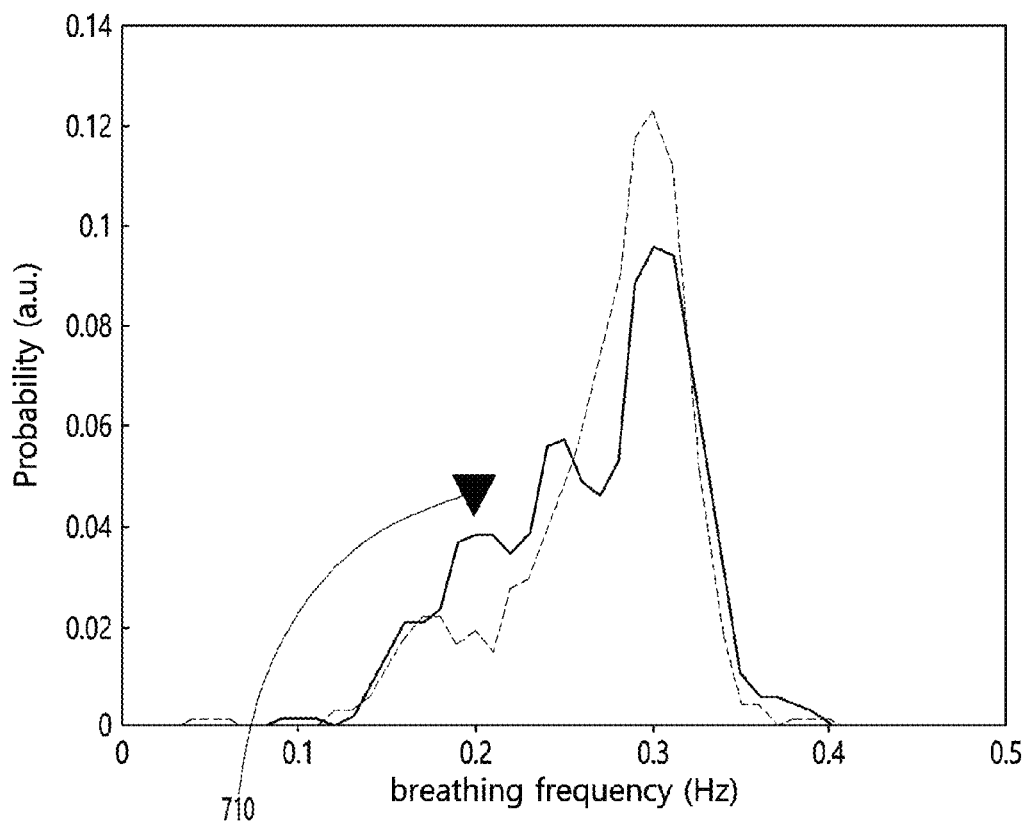
FIGS. 7 and 8 are diagrams showing experimental results according to the present disclosure.
Figure 8:
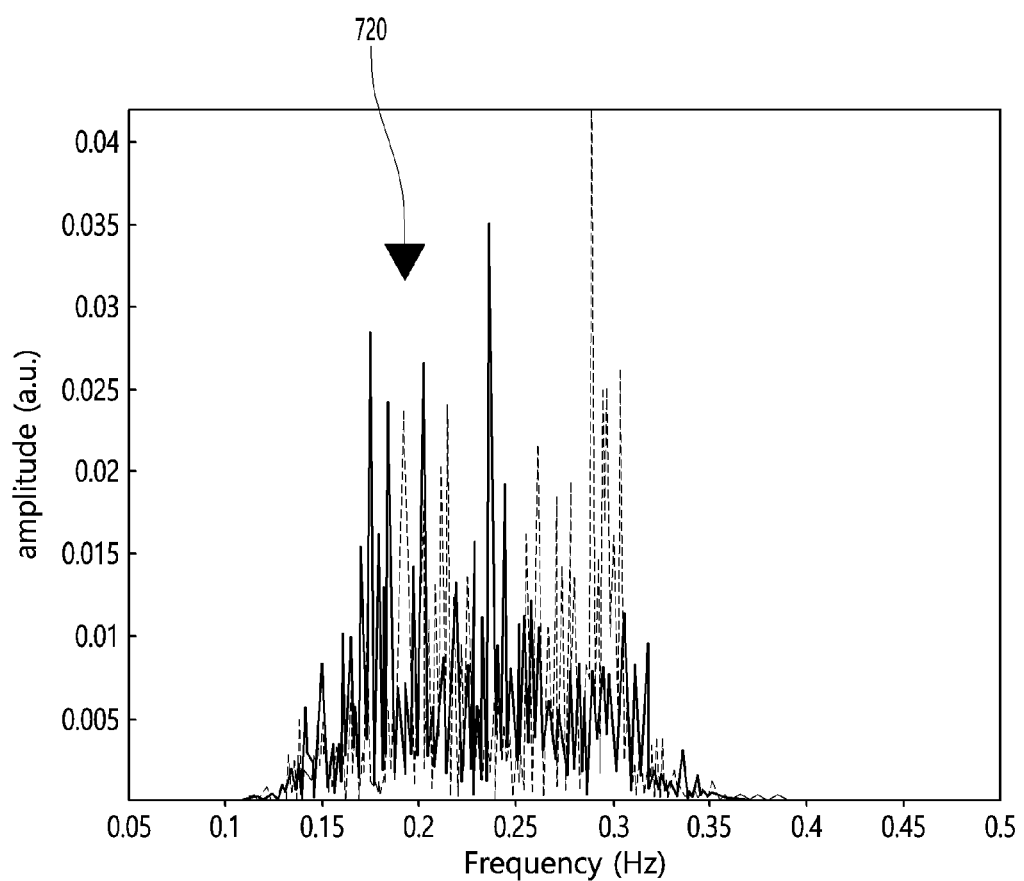

FIGS. 7 and 8 are diagrams showing experimental results according to the present disclosure.

In the graph of FIG. 7, the x-axis represents the user's breathing frequency. Also, the y-axis represents the frequency with which the user's breathing frequency appears.

The solid line represents the user's breathing frequency when the breathing-tuned sound is played, and the dotted line represents the user's breathing frequency when the breathing-tuned sound is not played.

In addition, the position of the arrow 710 represents the magnitude of the characteristic frequency.

Referring to FIG. 7, it can be seen that the frequency with which the user's actual breathing frequency is similar to the characteristic frequency (0.2 Hz) is much higher in the solid line than the dotted line.

This indicates that the user's actual breathing was induced similarly to the characteristic frequency of the breathing-tuned sound when the breathing-tuned sound was played.

Also, it can be seen that the overall frequency of low frequencies is higher in the solid line than the dotted line.

This represents that when the breathing-tuned sound is played, the user's actual breathing frequency becomes smaller according to the breathing-tuned sound.

The y-axis of the graph of FIG. 8 represents, using amplitudes, the frequency with which the user's breathing frequency appears.

The solid line represents the user's breathing frequency when the breathing-tuned sound is played, and the dotted line represents the user's breathing frequency when the breathing-tuned sound is not played.

Referring to FIG. 8, when the breathing-tuned sound is returned, the user's actual breathing is induced similarly to the characteristic frequency 720 of the breathing-tuned sound, and the user's actual breathing frequency decreases according to the breathing-tuned sound.

The present invention described above may be embodied as computer readable codes on a medium in which a program is recorded. The computer-readable medium includes all kinds of recording devices in which data readable by a computer system is stored. Examples of the computer readable medium may include a hard disk drive (HDD), a solid state disk (SSD), a silicon disk drive (SDD), a ROM, a RAM, a CD-ROM, a magnetic tape, a floppy disk, an optical data storage device, and the like. In addition, the computer may include a processor 180.

The invention claimed is:

1. A sleep induction device comprising:
   a speaker configured to output sound;
   a sensor configured to obtain a breathing signal of a user; and
   a processor configured to:
   obtain a breathing frequency of the user per a first time period based on the obtained breathing signal;
   determine and generate a breathing-tuned sound according to a characteristic frequency by combining a breathing induction signal with an ambient noise masking sound, wherein the characteristic frequency of the breathing-tuned sound including the ambient noise masking sound is determined according to a characteristic of the breathing induction signal; and
   output the breathing-tuned sound for inducing sleep in the user by inducing the user's breathing while simultaneously reducing the ambient noise,
   wherein the characteristic of the breathing induction signal corresponds to a magnitude of the obtained breathing signal or a frequency of the obtained breathing signal for a second time period.

2. The sleep induction device of claim 1, wherein the characteristic frequency of the breathing tuned sound is less than the obtained breathing frequency.

3. The sleep induction device of claim 2, wherein a difference between the characteristic frequency and the obtained breathing frequency is maintained at a preset value.

4. The sleep induction device of claim 1, wherein the processor is further configured to:
   output the breathing-tuned sound according to the characteristic frequency being a first frequency,
   reduce the frequency of the breathing-tuned sound from the first frequency to a second frequency based on the obtained breathing frequency, wherein the second frequency is less than the first frequency, and
   output the breathing-tuned sound according to the second frequency.

5. The sleep induction device of claim 4, wherein the processor is further configured to determine a point in time at which the characteristic frequency changes from the first frequency to the second frequency based on the obtained breathing frequency.

6. The sleep induction device of claim 5, wherein
   the breathing-tuned sound is output according to the second frequency based on a difference between the obtained breathing frequency and the first frequency becoming smaller than a predetermined magnitude.

7. The sleep induction device of claim 5, wherein the processor is further configured to
   output the breathing-tuned sound according to the second frequency based on the obtained breathing frequency decreasing to the first frequency.

8. The sleep induction device of claim 4, wherein the processor is further configured to
   output the breathing-tuned sound according to the second frequency based on a preset time elapsing since the breathing-tuned sound is output according to the first frequency.

9. The sleep induction device of claim 1, wherein the processor is further configured to:
   provide the obtained breathing frequency as an input to a reinforcement learning model,
   output the breathing-tuned sound according to at least one of a point in time at which the characteristic frequency recommended by the reinforcement learning model changes or a delta in the characteristic frequency, and
   train the reinforcement learning model using a reaction of the user.

10. The sleep induction device of claim 9, wherein the reaction of the user comprises at least one of a change in the breathing frequency, a movement of the user, or a time required for the user to enter a sleep state.

11. The sleep induction device of claim 1, wherein a minimum value of the characteristic frequency corresponds to the breathing frequency obtained during a sleep state of the user.

12. The sleep induction device of claim 1, wherein the processor is further configured to adjust a maximum magnitude of the breathing-tuned sound based on environment information determined by the processor.

13. The sleep induction device of claim 1, wherein the processor is further configured to:
provide the breathing frequency and environment information as an input to a reinforcement learning model,
output the breathing-tuned sound according to at least one of a point in time at which the characteristic frequency recommended by the reinforcement learning model changes, a delta in the characteristic frequency, a maximum magnitude of the breathing-tuned sound, or a type of the breathing-tuned sound, and
train the reinforcement learning model using a reaction of the user.

14. A method for operating a sleep induction device, the method comprising:
obtaining a breathing signal of a user by a sensor of the device;
obtaining, by a processor of the device, a breathing frequency of the user per a first time period based on the obtained breathing signal;
determining and generating, by the processor, a breathing-tuned sound according to a characteristic frequency by combining a breathing induction signal with an ambient noise masking sound, wherein the characteristic frequency of the breathing-tuned sound including the ambient noise masking sound corresponds to a characteristic of the breathing induction signal; and
outputting, by a speaker of the device, the breathing-tuned sound for inducing sleep in the user by inducing the user's breathing while simultaneously reducing the ambient noise,
wherein the characteristic of the breathing induction signal corresponds to a magnitude of the breathing induction signal or a frequency of the breathing induction signal for a second time period.

* * * * *